(12) United States Patent
Ogawa et al.

(10) Patent No.: US 7,508,526 B2
(45) Date of Patent: Mar. 24, 2009

(54) DEFECT INSPECTING APPARATUS

(75) Inventors: Riki Ogawa, Kawasaki (JP); Toru Tojo, Naka-gun (JP); Munehiro Ogasawara, Hiratsuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 262 days.

(21) Appl. No.: 11/249,359

(22) Filed: Oct. 14, 2005

(65) Prior Publication Data
US 2006/0082782 A1   Apr. 20, 2006

(30) Foreign Application Priority Data
Oct. 14, 2004   (JP)   ............... 2004-300266

(51) Int. Cl.
*G01B 9/02* (2006.01)
*G01B 11/02* (2006.01)

(52) U.S. Cl. ...................... 356/491; 356/511

(58) Field of Classification Search ............ 356/489, 356/511–516, 495, 237.2, 364, 491, 492
See application file for complete search history.

(56) References Cited

U.S. PATENT DOCUMENTS

| | | | | |
|---|---|---|---|---|
| 4,512,661 | A * | 4/1985 | Claus et al. | 356/493 |
| 4,795,246 | A * | 1/1989 | Lord | 359/371 |
| 5,764,363 | A * | 6/1998 | Ooki et al. | 356/364 |
| 5,790,251 | A * | 8/1998 | Hagiwara | 356/491 |
| 5,914,782 | A * | 6/1999 | Sugiyama | 356/491 |
| 5,969,855 | A * | 10/1999 | Ishiwata et al. | 359/386 |
| 6,025,956 | A * | 2/2000 | Nagano et al. | 359/386 |
| 6,433,876 | B1 * | 8/2002 | Kuhn | 356/516 |
| 6,525,875 | B1 * | 2/2003 | Lauer | 359/371 |
| 6,674,574 | B1 * | 1/2004 | Aono | 359/383 |
| 6,829,054 | B2 * | 12/2004 | Stanke et al. | 356/601 |
| 2004/0080757 | A1 * | 4/2004 | Stanke et al. | 356/601 |
| 2004/0252296 | A1 | 12/2004 | Tojo et al. | |
| 2005/0002020 | A1 | 1/2005 | Inoue et al. | |
| 2006/0103923 | A1 * | 5/2006 | Dietrich et al. | 359/385 |

FOREIGN PATENT DOCUMENTS

| | | |
|---|---|---|
| JP | 05-303040 | 11/1993 |
| JP | 2002-145902 | 6/1996 |
| JP | 10-177246 | 6/1998 |
| JP | 2002-267932 | 9/2002 |

OTHER PUBLICATIONS

U.S. Appl. No. 11/248,124, filed Oct. 13, 2005, to Ogawa et al.
English Translation of Copy of Notice of Reasons for Rejection mailed by Japan Patent Office in corresponding Japan Patent Application No. 2004-300266 on Jun. 17, 2008.

* cited by examiner

*Primary Examiner*—Patrick J Connolly
*Assistant Examiner*—Scott M Richey
(74) *Attorney, Agent, or Firm*—Finnegan, Henderson, Farabow, Garrett & Dunner, L.L.P.

(57) ABSTRACT

In a defect inspecting apparatus, a differential interference optical system forms a differential interference image which is produced from an optical interference of images in a predetermined direction, the images corresponding to inspecting parts of a pattern formed on a mask. A control part varies the predetermined direction so as to cause the differential interference optical system to produce another differential interference image. An image pickup sensor picks up the differential interference images in accordance with the variation of the predetermined direction. A defect detecting unit detects a defect in the pattern formed on the mask from comparing the differential interference images with reference images, respectively.

10 Claims, 5 Drawing Sheets

DEFECT INSPECTING APPARATUS

CROSS-REFERENCE TO RELATED APPLICATIONS

This application is based upon and claims the benefit of priority from prior Japanese Patent Application No. 2004-300266, filed Oct. 14, 2004, the entire contents of which are incorporated herein by reference.

BACKGROUND OF THE INVENTION

1. Field of the Invention

The present invention relates to an apparatus which inspects for defects, and in particular, to an apparatus that inspects a mask pattern for defects.

2. Description of the Related Art

With an increase in the degree of integration of semiconductor devices such as LSIs, efforts are being made to reduce the sizes of mask patterns formed on masks such as reticles. This requires high performance to be exhibited by defect inspecting apparatuses that inspect a pattern created on a mask for defects. However, it is not always easy to implement a high-performance defect inspecting apparatus.

The problems described below may occur in the inspection of a mask pattern for defects, for example, in the inspection of a mask pattern in which the phase of an optical wave shifts on a mask in accordance with a pattern. Masks on which a phase shift occurs include those in which a shift material that shifts phase is formed in a shifter section that shifts the phase of an optical wave, to provide the shifter section with a phase difference of $\lambda/2$, and those in which a glass substrate is trenched in the shifter section to provide the shifter section with a phase difference of $\lambda/2$. In particular, in the trench type phase shift mask, a trench region has almost the same transmittance as that of an un-trenched region. Accordingly, it is difficult to increase the contrast of the boundary between the trench region and the un-trenched region. Therefore, it is necessarily difficult to increase the detection sensitivity of the defect inspecting apparatus.

In connection with this problem, Jpn. Pat, Appln. KOKAI Publication No. 10-177246 proposes a defect inspecting apparatus utilizing a differential interference optical system. The differential interference optical system is implemented utilizing a birefringence prism that separates a bundle of light rays into smaller bundles separated from each other by a very small angle. Specifically, the birefringence prism separates a bundle of transmitted light rays or reflected light rays from a mask into a bundle of ordinary rays and a bundle extraordinary rays separated from each other by a very small angle. The two bundles of light rays resulting from the separation interfere with each other at an image formed surface. The intensities of the bundles of light rays vary depending on a phase difference. Since the phase difference between the trench region and un-trenched region of the phase shift mask is $\lambda/2$, the intensity varies significantly at the boundary between the trench region and the un-trenched region. Consequently, the boundary of the shifter section can be extracted very sensitively.

With the above method, if a separating direction, that is, a differential direction, at the birefringence prism is perpendicular to the boundary line between the trench region and the un-trenched region, the differential interference effect significantly varies the intensity at the boundary line. This enables the boundary to be detected very sensitively. However, if the bundle-of-light-ray separating direction is parallel to the boundary line, the intensity does not vary at the boundary line. This prevents the boundary line from being detected. Thus, it is difficult to very sensitively detect all the boundaries between the trench regions and the un-trenched regions using the above method. Disadvantageously, it is difficult to reliably detect defects in the shifter boundary for all the directions.

As described above, a problem with the conventional mask pattern defect inspecting apparatus is that it is difficult to reliably detect defects in a pattern for all the directions.

BRIEF SUMMARY OF THE INVENTION

It is an object of the present invention to provide a defect inspecting apparatus that can reliably detect defects in a phase difference pattern.

According to an aspect of the present invention, there is provided a defect inspecting apparatus comprising:

a differential interference optical system configured to form a differential interference image which is produced from an optical interference of images, the images being formed by first and second light ray components which are separated in a predetermined direction and emerged from the optical system, and corresponding to inspecting part of a pattern formed on a mask;

a control part configured to varies the predetermined direction so as to cause the differential interference optical system to produce an another differential interference image;

an image pickup sensor configured to pick up the differential interference images in accordance with the variation of the predetermined direction; and a defect detecting unit configured to detect a defect in the pattern formed on the mask from comparing the differential interference images with reference images, respectively.

According to another aspect of the present invention, there is provided a defect inspecting apparatus comprising:

a differential interference optical system configured to form first and second differential interference images, the first differential interference image being produced from a first optical interference of first images, and the second differential interference image being produced from a second optical interference of second images, the first image being formed by first and second light ray components which are separated in a first predetermined direction and emerged from the optical system, the second image being formed by third and fourth light ray components which are separated in a second predetermined direction and emerged from the optical system, and the first and second images corresponding to an inspecting part of a pattern formed on a mask;

first and second image pickup sensors configured to pick up the first and second differential interference images; and a defect detecting unit configured to detect a defect in the pattern formed on the mask from comparing the first and second differential interference images with first and second reference images, respectively.

According to yet another aspect of the present invention, there is provided a method of inspecting a defect, comprising:

forming a differential interference image which is produced from an optical interference of images, the images being formed by first and second light ray components which are separated in a predetermined direction, and corresponding to inspecting part of a pattern formed on a mask;

varying the predetermined direction so as to cause the differential interference optical system to produce an another differential interference image;

picking up the differential interference images in accordance with the variation of the predetermined direction; and detecting a defect in the pattern formed on the mask from comparing the differential interference images with reference images, respectively.

According to further aspect of the present invention, there is provided a method of inspecting a defect, comprising:

forming first and second differential interference images, the first differential interference image being produced from a first optical interference of first images, and the second differential interference image being produced from a second optical interference of second images, the first image being formed by first and second light ray components which are separated in a first predetermined direction and emerged from the optical system, the second image being formed by third and fourth light ray components which are separated in a second predetermined direction and emerged from the optical system, and the first and second images corresponding to an inspecting part of a pattern formed on a mask;

picking up the first and second differential interference images; and detecting a defect in the pattern formed on the mask from comparing the first and second differential interference images with first and second reference images, respectively.

DETAILED DESCRIPTION OF THE INVENTION

Figure 1:
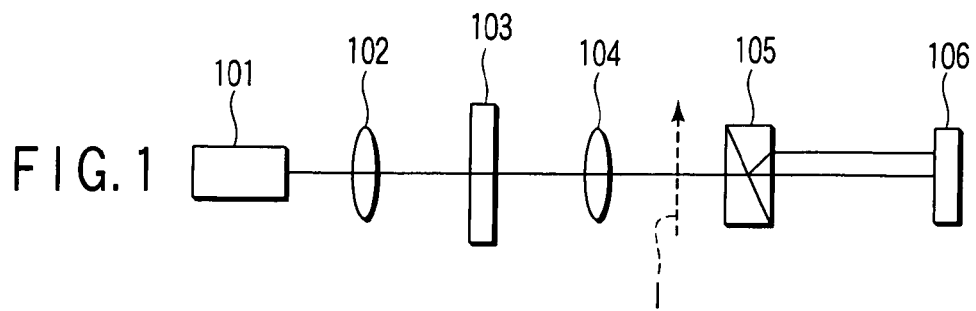
FIG. 1 is a diagram schematically showing a basic differential interference optical system applied to a defect inspecting apparatus in accordance with the present invention to acquire a differential. interference image.

With reference to the drawings, description will be given of a defect inspecting apparatus that inspects for defects according to an embodiment of the present invention The defect inspecting apparatus in accordance with the embodiment of the present invention utilizes a differential interference optical system to inspect a mask pattern for defects. First, with reference to FIGS. 1 and 2A to 2C, description will be given of the principle of acquisition of a differential interference image in the differential interference optical system. FIG. 1 is a diagram schematically showing the differential interference optical system.

A light source 101 shown in FIG. 1 emits illumination light rays, with which a mask, for example, a reticle 103, is illuminated via an optical system 102. A transmitted optical beam from the mask 103 is incident on a birefringence prism 105 placed at the position of the pupil, via an optical system 104. The birefringence prism 105 comprises a reflection surface that separates the incident light rays into a bundle of ordinary rays and a bundle of extraordinary rays. At the reflection surface of the birefringence prism 105, the ordinary rays contained in the incident light rays are not reflected but travel straight. The bundle of extraordinary rays is reflected at a very small angle to the bundle of ordinary rays; the extraordinary rays are contained in the incident light rays incident at the same incident point as that of the ordinary rays. Here, in the surface in which the incident light rays is separated into the bundle of ordinary rays and the bundle of extraordinary rays, a direction orthogonal to the optical axis is referred to as a differential direction I. The two bundles of light rays resulting from the separation at the reflection surface of the birefringence prism 105 are incident on an image pickup element 106. The two bundles of light rays resulting from the separation by the birefringence prism 105 form mask pattern images on an image formed surface so that the mask pattern images are shifted from each other. The light rays forming the two mask pattern images interfere with each other to create a differential interference image, which is picked up by the image pickup element 1.

Figure 2A:
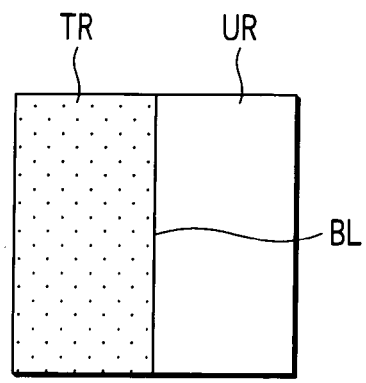
FIGS. 2A, 2B, 2C are diagrams illustrating the principle of acquisition of a differential interference image in the optical system shown in FIG. 1.
Figure 2B:
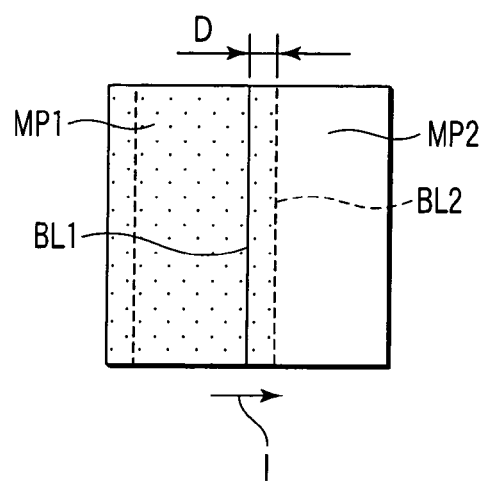
Figure 2C:
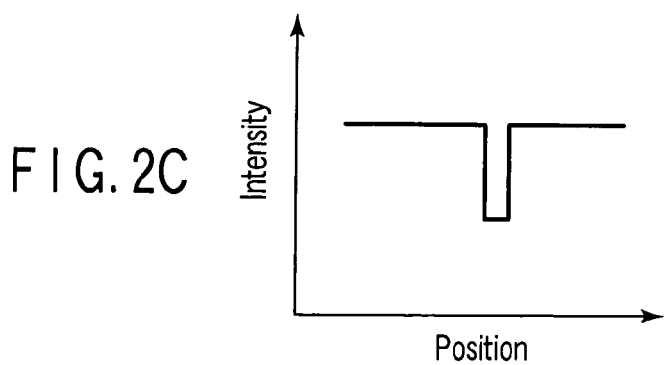

For example, as shown in FIG. 2A, it is assumed that a mask 103 that is a phase shift mask having a trench region TR and an un-trenched region UR is inspected; the trench region TR has its surface trenched and is flat and the un-trenched region UR has a height of $\lambda/2$ compared to the trench region, is in contact with the trench region via a boundary line BL, and corresponds to a mask surface. If the bundle-of-light-ray separating direction, that is, the differential direction I, at the birefringence prism 105 is perpendicular to the boundary line BL between the trench region and the un-trenched region, a differential interference image such as the one shown in FIG. 2B is formed on an image pickup surface of the image pickup element 106. That is, the two bundles of light rays resulting from the separation by the birefringence prism 105 form a first and second mask pattern images MP1 and MP2 on the image pickup surface which are displaced from each other by a displacement amount D. Since the phase difference between the trench region TR and the un-trenched region UR is $\lambda/2$, the differential interference effect causes the two bundles of light rays to interfere with each other at the boundary line BL to significantly vary light intensity as shown in FIG. 2C. This enables the boundary line BL to be detected more sensitively.

If an optical system such as the one shown in FIG. 1 is used, the birefringence prism 105 separates each of the light rays having passed through the corresponding point on the mask surface, i.e., the pattern formed surface, of the mask 103, into two light rays. The resulting light rays are formed into images at different points on the image pickup surface of the image pickup element 106. Accordingly, the light source 101 must generate coherent optical waves, i.e., laser beams.

To allow the light source 101 to generate coherent optical waves, a birefringence prism different from the birefringence prism 105 may be provided between the light source 101 and the mask 103. In this optical system, the birefringence prism provided between the light source 101 and the mask 103 separates a bundle of light rays from the light source 101 into two bundles of light rays, which are directed to the mask 103. The birefringence prism 105, provided between the mask 103 and the image pickup element 106, then synthesizes the two bundles of light rays transmitted through the mask 103 into one bundle of light rays again. An image resulting from the one bundle of light rays obtained is then formed on the image pickup element 106. Consequently, if the birefringence prisms are provided between the light source 101 and the mask 103 and between the mask 103 and the image pickup element 106, a differential interference image as shown in FIG. 2B can be obtained using even incoherent optical waves.

However, not all the boundary lines can be reliably detected simply by using the differential interference optical system shown in FIG. 1. That is, if the boundary line BL is parallel to the bundle-of-light-ray separating direction I, the light intensity does not vary at the boundary line BL. Consequently, it is not possible to sensitively detect any defects in the boundary line BL. Thus, defects in the boundary line BL can be reliably detected by using an arrangement such as the one described below in the embodiments of the present invention.

EMBODIMENT 1

Figure 3:
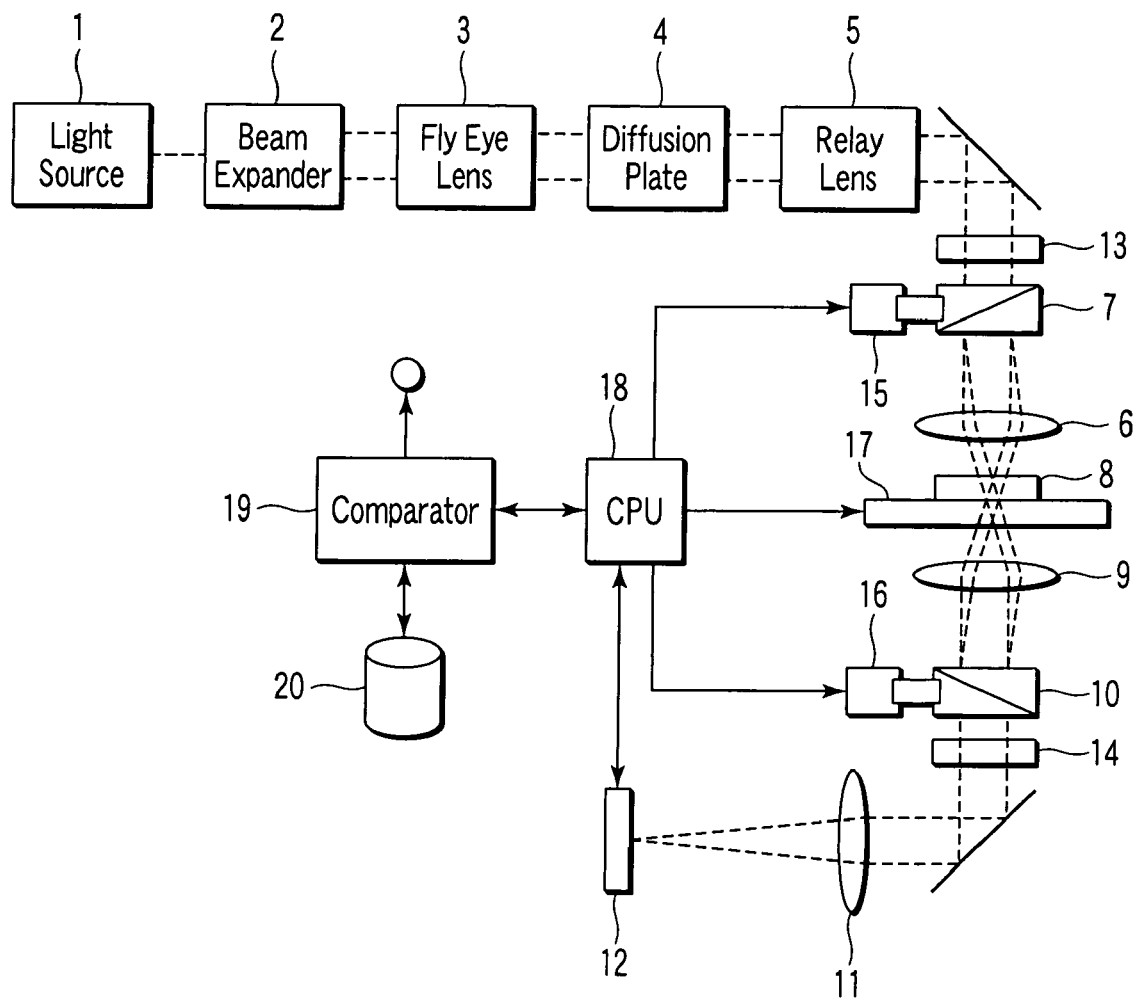
FIG. 3 is a block diagram schematically showing a defect inspecting apparatus in accordance with a first embodiment of the present invention.

FIG. 3 is a block diagram showing a defect inspecting apparatus according to a first embodiment of the present invention. The defect inspecting apparatus shown in FIG. 3 can temporally vary the direction in which the differential interference optical system exerts a differential interference effect to detect the boundary line BL, which may be formed in the surface of the mask pattern in various directions.

The light source 1 may generate either coherent optical waves or incoherent optical waves. The optical system shown in FIG. 3 uses a laser that generates coherent light. An illumination optical system uniformly illuminates a mask surface, i.e., a pattern formed surface of a mask 6 such as a reticle on which a desired mask pattern is formed, with an optical beam, for example, a laser beam, emitted by the light source 1 shown in FIG. 3. To uniformly illuminate the mask surface, a Kohler illumination optical system is preferably used as an illumination optical system.

A mask 8 is a substrate trenched type phase shift mask having the trench region TR and the un-trenched region UR as shown in FIG. 2A. In the illumination optical system, the following are arranged on an optical path: a beam expander, i.e., collimator lens 2, which expands or collimates an optical beam from the light source 1, and a fly eye lens, i.e., a compound eye lens 3, in which a large number of segment lenses having the same lens power are two-dimensionally arranged. Moreover, the following are arranged on the optical path of the optical system: an optical element, for example, a diffusion plate, which suppresses the interference between the components of the optical beam, i.e., the laser beam, and a condenser lens 6 that converges the optical beam, i.e., the laser beam, toward the mask surface. In the illumination optical system, a collimated optical beam from the light source 1 is incident on the fly eye lens 3, which converges the optical beam to form a plurality of convergence points. The diffusion plate 4 diffuses a plurality of beam components diverged from the plurality of convergence points. The diffused beam components are incident on the condenser lens 6 via a relay lens 5. The condenser lens 9 then collimates and directs the beam components to the mask surface. The condenser lens 6 has a focal point on the convergence points of the fly eye lens 3. Accordingly, images of light emitting points of the light source 1 are formed at the respective convergence points. Light rays from the light emitting point images are directed to the mask surface via the relay lens 5. Consequently, the mask surface is uniformly illuminated with the light rays. The optical element 4 reduces interference noise caused by Köhler illumination. Further, the relay lens 5 transmits a light source image to the mask surface. The condenser lens 6 forms the light source image on the mask surface. Consequently, the mask 8 is uniformly irradiated with the Köhler illumination.

The birefringence prison 7 separates a bundle of incident light rays into smaller bundles of light rays and emits the resulting bundles. The pattern formed surface of the mask 8 is illuminated with the bundles of light rays resulting from the separation by the birefringence prism 7. The birefringence prism 7 may be, for example, a Nomarski prism or a Wollaston polarizing prism.

The light rays transmitted through the mask 8 are incident on an objective lens 9 that corrects the light rays to direct the light rays to the a focal point. The objective lens 9 emits collimated optical waves. A birefringence prism 10 is placed at the pupil position of the objective lens 9. The birefringence prism 10 converts the two bundles of light rays resulting from the separation by the birefringence prism 7, back into one bundle of light rays. Like the birefringence prism 7, the birefringence prism 10 may be a Nomarski prism, a Wollaston polarizing prism, or the like. The bundle of light rays from the birefringence prism 10 is incident on the image pickup element 12 via an image forming lens 11. Consequently, a differential interference image, for example, the one shown in FIG. 2B, is formed on the image pickup surface of the image pickup element 12.

In a mask having a phase shift pattern, the boundary line BL of a shifter region that provides a phase difference varies discontinuously. Accordingly, a desired contrast can be obtained at the boundary line even if a sheer degree D determined by the bundle-of-light-ray separating angle of the birefringence prism 7 or 10, i.e., the displacement amount of the bundles of light rays on the mask surface, is smaller than the value of resolution of the optical system in the defect inspecting apparatus.

In the example shown in FIG. 3, polarizing plates 13 and 14 can be provided immediately before the birefringence prism 7 and immediately after the birefringence prism 10 to remove unwanted polarizing components.

In the optical system shown in FIG. 3, the birefringence prisms 7 and 10 are rotated around the optical axes of the corresponding optical systems by spindle motors 15 and 16, respectively. The rotation speeds and phases of the spindle motors 15 and 16 are controlled using encoder pulses. The birefringence prisms 7 and 10 are thus rotated in synchronism with each other. By rotating the birefringence prisms 7 and 10 during the image pickup period, i.e., the exposure period, of the image pickup element 12, it is possible to temporally vary the bundle-of-light-ray separating direction of the birefringence prisms 7 and 10, i.e., the direction I in which the differential interference effect is exerted. This temporally varies the relationship between the bundle-of-light-ray separating direction and the boundary line between the trench region and the un-trenched region. As a result, the differential interference effect can be reliably exerted on each boundary line BL which may be extended on the mask surface in any of various directions.

As in inspecting operation is started, a stage 17 on which a mask 8 is placed is driven. The mask 8 is thus moved along a plane (xy plane) orthogonal to the optical axis of the optical system. The mask 8 is scanned by a bundle of light rays. Consequently, the entire mask surface is inspected by the bundle of light rays. Specifically, the stage 17 is first continuously moved in an x direction from the end to end of an inspection region to scan the mask. Subsequently, the stage 17 is moved step by step in a y direction orthogonal to the x direction, and is then continuously moved in a −x direction to scan the mask. A differential interference image of the entire inspection region of the mask is obtained by thus repeating the continuous scan in the x direction and the step movement in the y direction.

The image pickup element 12 is of, for example, a TDI (Time Delay Integration) type; charges generated in the image pickup element 12 are transferred along the direction in which the mask is continuously moved. A charge transfer timing is precisely adjusted to the speed at which the stage is moved. The need for a shutter is eliminated by combining the continuous movement of the stage and the TDI operation. Further, accumulation of charges enables sensitive detections.

The following time corresponds to the product of the TDI transfer speed and the number of accumulation stages: the time required for the image pickup element 12 to carry out exposure enough to obtain data for one line. The spindle motors 15 and 16 are driven so as to rotate the birefringence prisms 7 and 10 once during the exposure time. Thus, a host computer (CPU) 18 synchronously controls the driving of the spindle motors 15 and 16, the movement of the stage 17, and the TDI operation. As a result, differential interference images can be obtained for all the directions.

The differential interference image picked up by the image pickup element 12 is sent to a comparator 19, which then compares the differential interference image with a reference image stored in a storage section 20. As a result, the difference between the differential interference image and the reference image is extracted as a defect in the mask pattern.

In die-to-die inspections, the reference image is an image of a pattern on the same mask which is acquired beforehand. Specifically, first, an image obtained from a certain pattern on the mask is saved to the storage section 20 as a reference image. Subsequently, a different pattern is acquired as described above, the different pattern being formed on the same mask on which the above pattern is formed and having the same shape as that of the above pattern. Further, the comparing section 19 compares the image acquired with the image saved to the storage section 20.

The above technique is applicable not only to the die-to-die inspections but also to die-to-database inspections. In the die-to-database inspection, image data on an image acquired as described above is compared with mask pattern data to extract a defect in the mask pattern.

As described above, according to the present embodiment, the birefringence prisms are rotated to temporally vary the bundle-of-light-ray separating direction of the birefringence prisms and thus the direction in which the differential interference optical system exerts a differential interference effect. Thus, the picked-up image is the average of the differential interference images obtained for all the directions. Consequently, the differential interference images for all the directions can be acquired using one image. Therefore, at least a specified magnitude of variation in intensity is obtained at the shifter boundary line BL for all the directions. This makes it possible to reliably detect a defect in the mask pattern.

The above embodiment relates to the transmissive optical system that forms an optical beam transmitted through the mask into an image on the image pickup element. However, the above technique is equally applicable to a reflective optical system that forms an optical beam reflected by the mask into an image on the image pickup element.

Figure 4:
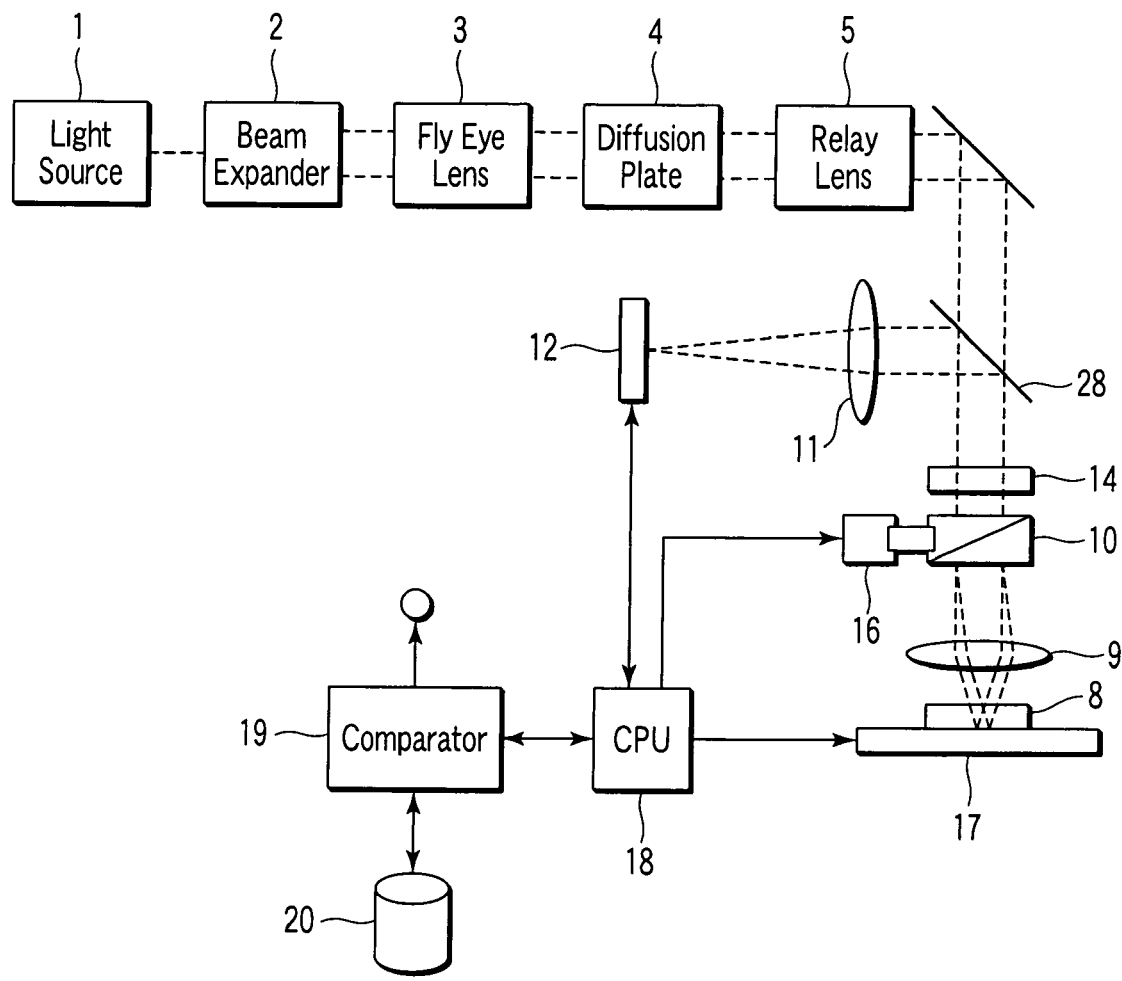
FIG. 4 is a block diagram showing a modification of the defect inspecting apparatus shown in FIG. 3.

FIG. 4 is a block diagram showing an example of a defect inspecting apparatus having a reflective optical system. The components corresponding to those shown in FIG. 3 have the same reference numerals and their detailed description is omitted.

The inspecting apparatus shown in FIG. 4 uses reflected light rays from the mask 8. Accordingly, one birefringence prism is used as both birefringence prisms 7 and 10 shown in FIG. 3. Further, in the reflective optical system, an optical path for illumination light rays must be separated from an optical path for reflected light rays. Accordingly, a half mirror 28 is provided in the optical paths for illumination light rays and for reflected light rays. That is, a bundle of illumination light rays is transmitted through the half mirror 28 and supplied to the birefringence prism 10, which then separates the bundle of illumination light rays into two bundles of light rays. These bundles of light rays are incident on the mask 8. The birefringence prism 10 converts the two bundles of light rays reflected by the mask 8 back into one bundle of light rays. The bundle of reflected light rays from the birefringence prism is reflected by the half mirror 28 and then enters the image pickup element 12.

Thus, also in the reflective optical system, by rotating the birefringence prism as in the case of the transmissive optical system shown in FIG. 3, it is possible to detect the boundary line BL which may be extended on the mask surface in any of various directions as in the case of the transmissive optical system shown in FIG. 3.

In the above embodiment, the birefringence prism 7 is provided on the illumination side, while the birefringence prism 10 is provided on the image formation side, as shown in FIG. 3. However, if the light source 1 generates coherent optical waves, the birefringence prism may be provided only on the image formation side. Also in this case, effects similar to those in the example shown in FIG. 3 can be exerted by rotating the birefringence prism as in the case of the example shown in FIG. 3.

In the above first embodiment and its variation, the birefringence prism is rotated once during the image pickup period (exposure period) of the image pickup element. However, the birefringence prism may generally be rotated n times (n is an integer). Further, the birefringence prism need not be continuously rotated during the image pickup period of the image pickup element. The birefringence prism may be controlled so that at least two bundle-of-light-ray separating directions (differential directions) are set for the birefringence prism during the image pickup period of the image pickup element.

EMBODIMENT 2

Figure 5:
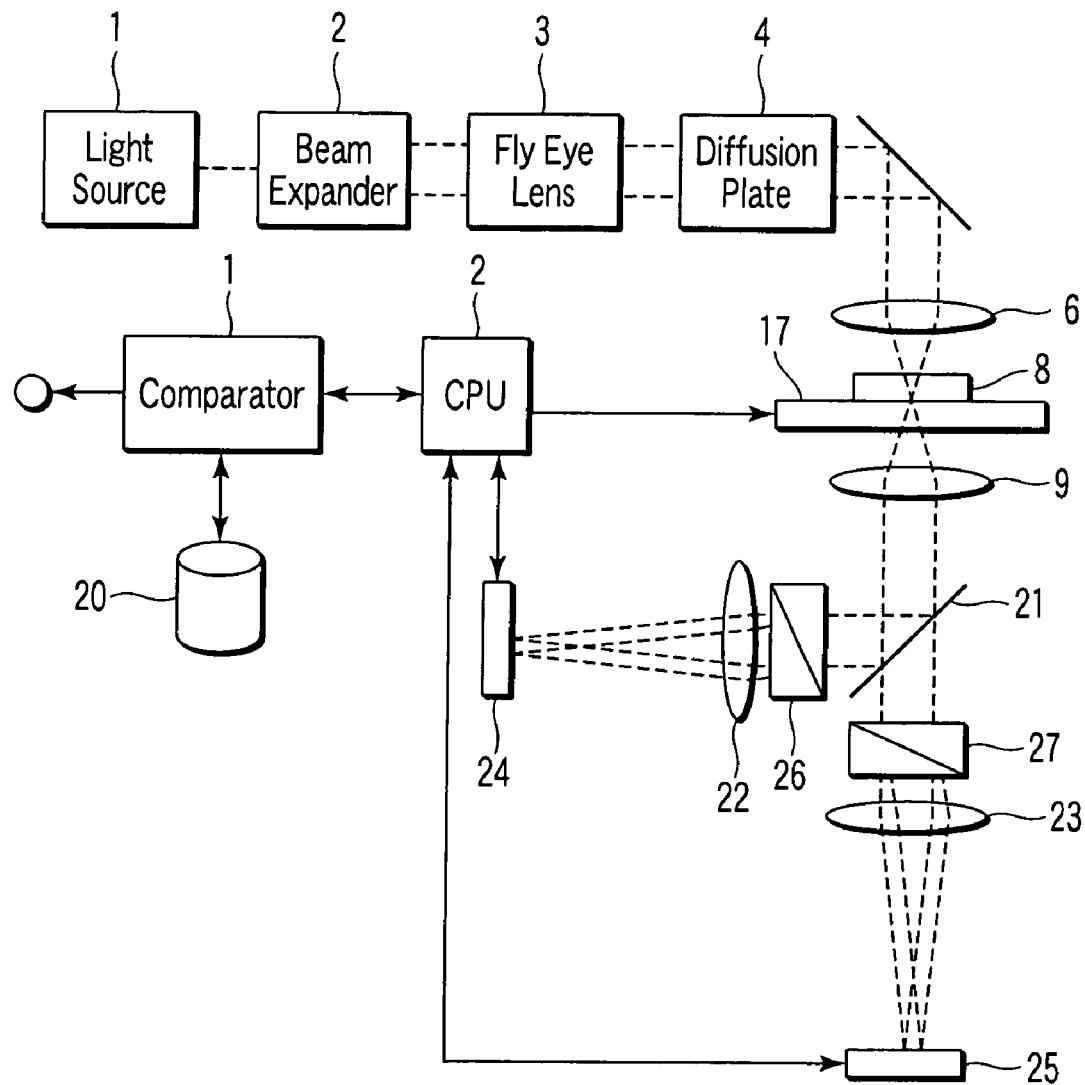
FIG. 5 is a block diagram showing a defect inspecting apparatus in accordance with a second embodiment of the present invention.

FIG. 5 is a block diagram showing an example of a defect inspecting apparatus in accordance with a second embodiment of the present invention. The present embodiment is provided with a plurality of differential interference optical systems that exert a differential interference effect in different directions I, and a plurality of image pickup sections. The components corresponding to those shown in FIG. 3 have the same reference numerals and their detailed description is omitted. A detailed description is also omitted for operations similar to those described in the first embodiment.

In the optical system shown in FIG. 5, the light source 1 is a laser that generates coherent light. An illumination optical system subjects the mask surface (pattern surface) of the mask 8 on which a desired pattern is formed, to Köhler illumination with a light rays emitted by the light source 1. The phase shift mask 8 is of a substrate trenched type having the trench region TR and the un-trenched region UR as shown in FIG. 2A. The illumination optical system includes the expander 2, the fly eye lens 3, an interference noise reducing element 4, and the condenser lens 6.

In the optical system shown in FIG. 5, light rays transmitted through the mask 8 are incident on the objective lens 9, which then emits parallel beams. A half mirror 21 then separates the bundle of light rays from the objective lens 9 into two bundles of light rays. One of the bundles of light rays resulting from the separation by the half mirror 21 is incident on a birefringence prism 26, which then separates this bundle of light rays into two bundles of light rays. These bundles of light rays are incident on an image pickup element 24 via an image forming lens 22. A differential interference image is thus formed on the image pickup surface of the image pickup element 24. The other bundle of light rays resulting from the separation by the half mirror 21 is incident on a birefringence prism 27, which then separates this bundle of light rays into two bundles of light rays. These bundles of light rays are similarly incident on an image pickup element 25 via an image forming lens 23. A differential interference image is thus formed on the image pickup surface of the image pickup element 25. The birefringence prisms 26 and 27 and the image pickup elements 24 and 25 may be basically similar to those shown in the first embodiment.

Both birefringence prisms 26 and 27 are arranged at the pupil position of the objective lens 9. Further, the birefringence prisms 26 and 27 are arranged so that their bundle-of-light-ray separating directions (differential directions) I are orthogonal to each other. For example, the birefringence prism 26 separates a bundle of light rays into two bundles of light rays corresponding to the x direction on the mask surface, i.e., the pattern formed surface, of the mask 8. The birefringence prism 27 separates a bundle of light rays into two bundles of light rays corresponding to the y direction on the mask surface. Thus, the image pickup element 24 provides a differential interference image obtained by differentiation in the x direction on the mask surface. The image pickup element 25 provides a differential interference image obtained by differentiation in the y direction on the mask surface.

The differential interference images picked up by the image pickup elements 24 and 25 are sent to the comparing section 19 via the host computer (CPU) 18. The comparing section 19 compares each of the differential interference images with the reference image stored in the storage section 20 as in the case of the first embodiment. As a result, the difference between each differential interference image and the reference image is extracted as a defect in the mask pattern. In the present example, each of the images picked up by the image pickup elements 24 and 25 must be compared with the reference image. Thus, the data on the reference image is provided for each of the images picked up by the image pickup elements 24 and 25. By thus comparing the reference image with each of the differential interference images obtained using the different differential directions, it is possible to acquire an intensity variation occurring at the shifter boundary line BL, at a specified sensitivity or higher for all the directions.

As described above, according to the present embodiment, by using a plurality of differential interference optical systems having different bundle-of-light-ray separating directions, it is possible to simultaneously acquire a plurality of differential interference images with different differential directions (directions in which a differential interference effect is exerted). Therefore, defects in the shifter boundary line can be acquired at the specified sensitivity or higher for all the directions. This enables defects in the mask pattern to be reliably detected.

The above embodiment relates to the transmissive optical system that forms an optical beam transmitted through the mask into an image on the image pickup element. However, the above technique is equally applicable to a reflective optical system that forms an optical beam reflected by the mask into an image on the image pickup element.

Figure 6:
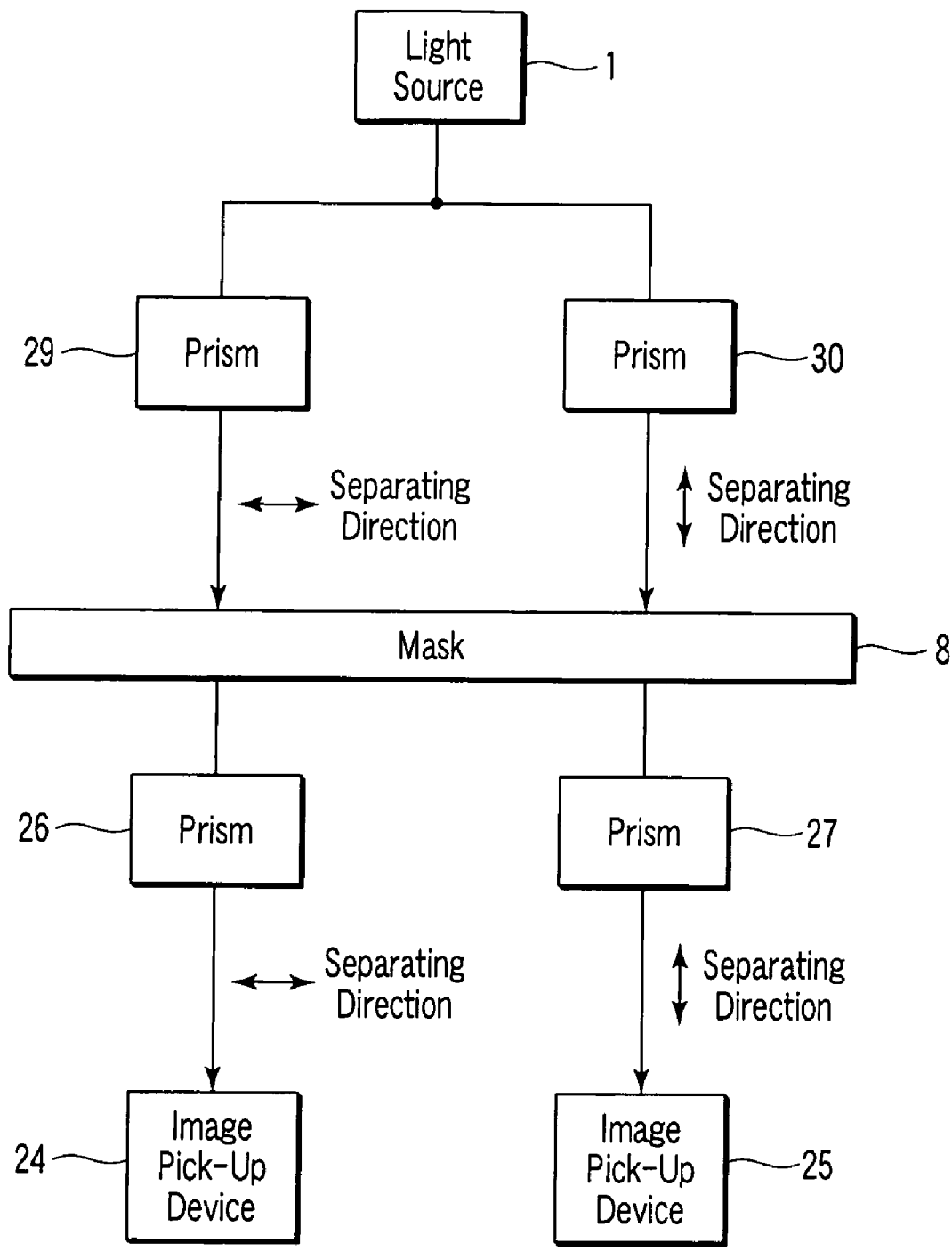
FIG. 6 is a block diagram schematically showing a modification of the defect inspecting apparatus shown in FIG. 5.

In the above embodiment, the birefringence prisms 26 and 27 are provided only on the image formation side, as shown in FIG. 5. However, by also providing two birefringence prisms on the illumination side, the light source 1 is allowed to generate incoherent optical waves. FIG. 6 is a block diagram schematically showing an arrangement adopting an optical system in which two birefringence prisms 29 and 30 are provided on the illumination side.

If such an arrangement is used, two illumination optical systems are provided in association with the birefringence prisms 29 and 30 on the illumination side. The illumination optical systems are configured so that on the mask surface, the illumination field of the first illumination optical system corresponding to the birefringence prism 29 is different from that of the second illumination optical system corresponding to the birefringence prism 30. Then, the first image formation optical system which corresponds to the birefringence prism 26, forms an image of the illumination field of the first illumination optical system. The second image formation optical system corresponding to the birefringence prism 27 forms an image of the illumination field of the second illumination optical system. The birefringence prisms 26 and 29 have the same bundle-of-light-ray separating direction. The birefringence prisms 27 and 30 have the same bundle-of-light-ray separating direction. The bundle-of-light-ray separating direction of the birefringence prisms 26 and 29 is orthogonal to that of the birefringence prisms 27 and 30.

The above arrangement can also exert effects similar to those in the example shown in FIG. 5.

In the above second embodiment and its variation, the angle between the bundle-of-light-ray separating directions (differential directions) of the two birefringence prisms need not necessarily be 90°. It is only necessary that the bundle-of-light-ray separating directions of the two birefringence prisms are different from each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for inspecting a defect in a pattern formed on a mask, comprising:
    a differential interference optical system having an optical axis, which includes:
        a first birefringence prism configured to separate light rays into first ordinary and extraordinary light ray components which are separated in a first predetermined direction and are directed to the mask, the first ordinary and extraordinary light ray components emerging from the mask forming a first differential interference image, and
        a second birefringence prism configured to separate light rays into second ordinary and extraordinary light ray components which are separated in a second predetermined direction different from the first predetermined direction and are directed to the mask, the second ordinary and extraordinary light ray components emerging from the mask forming a second differential interference image;
    first and second image pickup sensors configured to pick up the first and second differential interference images, respectively; and
    a defect detecting unit configured to detect a defect in the pattern formed on the mask by comparing the first and second differential interference images with first and second reference images, respectively.

2. The apparatus according to claim 1, wherein the differential interference optical system further includes:

a third birefringence prism configured to synthesize the first ordinary and extraordinary light ray components passing through the mask to form the first differential interference image; and a fourth birefringence prism configured to synthesize the second ordinary and extraordinary light ray components passing through the mask to form the second differential interference image.

3. An apparatus for inspecting a defect in a pattern formed in a phase shift mask, comprising:

an illumination optical system which irradiates the phase shift mask with illumination light rays;

an objective lens which converts the light rays transmitted through the phase shift mask to parallel light rays;

a half mirror which separates the parallel light rays into first and second light ray components;

a first birefringence prism which separate the first light ray component into first ordinary and extraordinary light rays at a small separation angle along a first differential direction;

a first pickup element having a first imaging surface on which a first differential interference image is produced from an first interference of the first ordinary and extraordinary light rays;

a second birefringence prism which separates the second light ray component into second ordinary and extraordinary light rays at a small separation angle along a second differential direction different from the first differential direction;

a second pickup element having a second imaging surface on which a second differential interference image is produced from an interference of the second ordinary and extraordinary light rays; and a comparator which compares the first and second interference images with a reference image to detect the defect.

4. The apparatus according to claim 3, wherein the first direction is orthogonal to the second direction.

5. An apparatus for inspecting a defect in a pattern formed in a phase shift mask, comprising:

a first illumination optical system including a first birefringence prism which separates a first illumination light ray component into first ordinary and extraordinary light rays at a small separation angle along a first differential direction, the first ordinary and extraordinary light rays being projected on a first illumination area of the phase shift mask;

a second illumination optical system including a second birefringence prism which separates a second illumination light ray component into second ordinary and extraordinary light rays at a small separation angle along a second differential direction different from the first differential direction, the second ordinary and extraordinary light rays being projected on a second area of the phase shift mask;

a first imaging optical system including a third birefringence prism which combines the first ordinary and extraordinary light rays passing through the phase shift mask, along the first differential direction, to produce a first combined light beam including a first differential interference image of the first illumination area;

a first pick-up element picking up the first differential interference image;

a second imaging optical system including a fourth birefringence prism which combines the second ordinary and extraordinary light rays passing through the phase shift mask, along the second differential direction, to produce a second combined light beam including a second differential interference image of the first illumination area, the first imaging optical system projecting the second light beam;

a second pick-up element picking up the second differential interference image;

a comparator comparing the first differential interference image with a first reference image and the second differential interference image with a second reference image to extract the defect in the pattern formed in a phase shift mask.

6. The apparatus according to claim 5, wherein the second differential direction is orthogonal to the first differential direction.

7. A method of inspecting a defect in a pattern formed in a phase shift mask, comprising:

irradiating the phase shift mask with illumination light rays;

converting the light rays transmitted through the phase shift mask to parallel light rays;

separating the parallel light rays into first and second light ray components;

separating the first light ray component into first ordinary and extraordinary light rays at a small separation angle along a first differential direction;

picking up a first differential interference image formed on a first imaging surface, the first differential interference image being produced from an first interference of the first ordinary and extraordinary light rays;

separating the second light ray component into second ordinary and extraordinary light rays at a small separation angle along a second differential direction different from the first differential direction;

picking up a second differential interference image formed on a second imaging surface, the second differential interference image being produced from an second interference of the second ordinary and extraordinary light rays; and comparing the first and second interference images with a reference image to detect the defect.

8. The method according to claim 7, wherein the first differential direction is orthogonal to the second direction.

9. A method of inspecting a defect in a pattern formed in a phase shift mask, comprising:

separating first illumination light ray component into first ordinary and extraordinary light rays at a small separation angle along a first differential direction, the first ordinary and extraordinary light rays being projected on a first illumination area of the phase shift mask;

separating a second illumination light ray component into second ordinary and extraordinary light rays at a small separation angle along a second differential direction different from the first differential direction, the second ordinary and extraordinary light rays being projected on a second area of the phase shift mask;

combining the first ordinary and extraordinary light rays passing through the phase shift mask, along the first differential direction, to produce a first combined light beam including a first differential interference image of the first illumination area;

picking up the first differential interference image;

combining the second ordinary and extraordinary light rays passing through the phase shift mask, along the second differential direction, to produce a second combined light beam including a second differential interference image of the first illumination area, the first imaging optical system projecting the second light beam;

picking up the second differential interference image; and comparing the first differential interference image with a first reference image and the second differential interference image with a second reference image to extract the defect in the pattern formed in a phase shift mask.

10. The method according to claim 9, wherein the second differential direction is orthogonal to the first differential direction.

* * * * *

UNITED STATES PATENT AND TRADEMARK OFFICE
CERTIFICATE OF CORRECTION

| | | |
|---|---|---|
| PATENT NO. | : 7,508,526 B2 | Page 1 of 1 |
| APPLICATION NO. | : 11/249359 | |
| DATED | : March 24, 2009 | |
| INVENTOR(S) | : Ogawa et al. | |

It is certified that error appears in the above-identified patent and that said Letters Patent is hereby corrected as shown below:

Claim 3, column 11, line 23, change "an first" to --a first--.

Claim 7, column 12, line 27, change "an first" to --a first--.

Claim 7, column 12, line 35, change "an second" to --a second--.

Signed and Sealed this

Seventh Day of July, 2009

JOHN DOLL
*Acting Director of the United States Patent and Trademark Office*